(12) United States Patent
Wood et al.

(10) Patent No.: US 7,247,475 B2
(45) Date of Patent: *Jul. 24, 2007

(54) METHOD FOR PRODUCING MONOCLONAL ANTIBODIES

(75) Inventors: Clive R. Wood, Boston, MA (US); Randal J. Kaufman, Ann Arbor, MI (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/324,255

(22) Filed: Jan. 4, 2006

(65) Prior Publication Data

US 2006/0141574 A1 Jun. 29, 2006

Related U.S. Application Data

(63) Continuation of application No. 10/244,894, filed on Sep. 17, 2002, now Pat. No. 7,011,974, which is a continuation of application No. 07/765,281, filed on Sep. 25, 1991, now Pat. No. 6,475,787, which is a continuation-in-part of application No. 07/386,489, filed on Jul. 28, 1989, now abandoned.

(51) Int. Cl.
*C12N 5/02* (2006.01)
*C12N 5/06* (2006.01)
*C12N 15/63* (2006.01)
*C12P 21/08* (2006.01)

(52) U.S. Cl. ............... 435/326; 435/6; 435/320.1; 435/325; 435/455; 435/449

(58) Field of Classification Search ............ None
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel | |
| 4,656,134 A | 4/1987 | Ringold | |
| 4,713,339 A | 12/1987 | Levinson et al. | |
| 4,816,387 A | 3/1989 | Boss | |
| 4,816,397 A | 3/1989 | Boss et al. | |
| 4,816,567 A | 3/1989 | Cabilly et al. | |
| 4,956,288 A | 9/1990 | Barsoum | |
| 5,179,017 A | 1/1993 | Axel | |
| 5,545,403 A | 8/1996 | Page | |
| 5,545,404 A | 8/1996 | Page | |
| 5,545,405 A | 8/1996 | Page | |
| 6,331,415 B1 | 12/2001 | Cabilly et al. | |
| 6,455,275 B1 | 9/2002 | Axel | |
| 6,475,787 B1 * | 11/2002 | Wood et al. | 435/326 |
| 7,011,974 B2 * | 3/2006 | Wood et al. | 435/326 |
| 2003/0153039 A1 | 8/2003 | Wood | |

FOREIGN PATENT DOCUMENTS

| | | |
|---|---|---|
| EP | 0481790 | 2/1999 |
| WO | WO 81/02426 | 9/1981 |
| WO | WO 88/08035 | 10/1988 |
| WO | WO 87/04187 | 7/1989 |

OTHER PUBLICATIONS

Barsoum et al., "Introduction of stable high-copy-number DNA into Chinese hamster ovary cells by electroporation," *DNA and Cell Biology* 9: 293-300 (1990).
Beidler et al., "Cloning and high level expression of a chimeric antibody with specificity for human carcinoembryonic antigen," *J. Immunol.* 141:4053-60 (1988).
Brennand et al., "Cloned cDNA sequences of the hypoxanthine/guanine phosphoribosyltransferase gene from a mouse neuroblastoma cell line found to have amplified genomic sequences," *Proc. Natl. Acad. Sci. USA* 79:1950-1954 (1982).
Brinkhous et al., "Purified human factor VIII procoagulant protein: Comparative hemostatic response after infusions into hemophilic and von Willebrand disease dogs," *Proc. Natl. Acad. Sci. USA* 82:8752-8756 (1985).
Dorai et al., "The effect of dihydrofolate reductase-mediated gene amplification of the expression of transfected immunoglobulin genes," *J. Immunol.* 139:4232-4241 (1987).
Goding et al., "Cellular basis of the immune system" in "Monoclonal antibodies: Principles and Practice," Third Edition-Academic Press Limited, London: 29-46 (1996).
Kaufman et al., "Control of translation initiation in mammalian cells," Genetic Engineering 9:155, J. K. Setlow, ed. (Plenum Publishing Corp.) 1987.
Kaufman et al., "Effect of von Willebrand factor coexpression on the synthesis and secretion of factor VIII in Chinese hamster ovary cells," *Mol and Cell Biol.* 9:1233-42 (1989).
Liu et al., "Production of a mouse-human chimeric monoclonal antibody to CD20 with potent Fc-dependent biologic activity," *J. Immunol.* 139:3521-3526 (1987).
Page et al., "High level expression of the humanized monoclonal antibody Campath-1H in Chinese hamster ovary cells," *Biotechnology* 9:64-68 (1991).
Schimke et al., "Gene amplification in cultured animal cells," *Cell* 37:705-713 (1984).
Toole, et al., "Molecular cloning of a cDNA encoding human antihaemophilic factor," *Nature* 312:342-347 (1984).
Verweij et al., "Full-length von Willebrand factor (vWF) cDNA encodes a highly positive protein larger than the mature vWF subunit," *EMBO J* 5:1839-1847 (1986).
Weide et al., "Reconstruction of functionally active antibody directed against creatine kinase from separately expressed heavy and light chains in non-lymphoid cells," *Gene* 51:21-29 (1982).
Wood et al., "Expression of active human factor VIII from recombinant DNA clones," *Nature* 312:330-337 (1984).
Wood et al., "High level synthesis of immunoglobulins in Chinese hamster ovary cells," *J. Immunol.* 145:3011-3016 (1990).

* cited by examiner

*Primary Examiner*—Anne Marie Wehbé
(74) *Attorney, Agent, or Firm*—Finnegan, Henderson, Farabow, Garrett & Dunner, L.L.P.

(57) ABSTRACT

An improved method for the production of monoclonal antibodies is disclosed.

20 Claims, No Drawings

SEQUENCE LISTING

<160> NUMBER OF SEQ ID NOS: 4

<210> SEQ ID NO 1
<211> LENGTH: 79
<212> TYPE: DNA
<213> ORGANISM: Artificial
<220> FEATURE:
<223> OTHER INFORMATION: leader sequence

<400> SEQUENCE: 1
aattcgtaat gggatggagc tgtatcatgc tcttcttggc agcaacagct acaggtgtcc      60
actcccaggt ccaactgca                                                  79

<210> SEQ ID NO 2
<211> LENGTH: 69
<212> TYPE: DNA
<213> ORGANISM: Artificial
<220> FEATURE:
<223> OTHER INFORMATION: leader sequence

<400> SEQUENCE: 2
gttgacctgg gagtggacac ctgtagctgt tgctgccaag aagagcatga tacagctcca      60
tcccattag                                                             69

<210> SEQ ID NO 3
<211> LENGTH: 20
<212> TYPE: DNA
<213> ORGANISM: Artificial
<220> FEATURE:
<223> OTHER INFORMATION: ligating oligodeoxyribonucleotide

<400> SEQUENCE: 3
tcgacgccat ggcctggatt                                                 20

<210> SEQ ID NO 4
<211> LENGTH: 21
<212> TYPE: DNA
<213> ORGANISM: Artificial
<220> FEATURE:
<223> OTHER INFORMATION: ligating oligodeoxyribonucleotide

<400> SEQUENCE: 4
gtgaaatcca ggccatggcc g                                               21

METHOD FOR PRODUCING MONOCLONAL ANTIBODIES

This is a continuation of U.S. patent application Ser. No. 10/244,894, now U.S. Pat. No. 7,011,974, filed Sep. 17, 2002, which is a continuation application of U.S. patent application Ser. No. 07/765,281, now U.S. Pat. No. 6,475,787, filed Sep. 25, 1991, which is a continuation-in-part of U.S. application Ser No. 07/386,489, filed on Jul. 28, 1989 (now abandoned). These applications are hereby incorporated by reference in their entirety.

This invention was made with government support under grant number R44GM37329-01-02-0379428 awarded by the Department of Health and Human Services. The U.S. government has certain rights in this invention.

The production of monoclonal antibodies using hybridoma cells is now well known in the art. Briefly, isolated antibody-producing lymphocytes from an immunized animal, typically a mouse, are fused with an immortalized cell line, and the resultant hybridomas are screened for the production of the desired monoclonal antibody. Such methods have been successfully used to produce a wide array of antibodies.

However, several inherent shortcomings limit the utility of such methods and the resultant monoclonal antibodies (MAbs). Foremost of those limitations is that the Mabs so produced are essentially murine in nature and reactivity. Use of murine MAbs in human patients, whether for diagnostic or perhaps especially for therapeutic or prophylactic use, incurs a risk of untoward antigenic response by the patient.

In order to avoid such antigenicity, genetically engineered antibodies have been produced which retain the specific antigen-binding domains of the parent murine antibody, while substituting corresponding human antibody domains for part or all of the remaining murine polypeptide regions. It is hoped that such antibodies will not prove antigenic in humans because of their greater resemblance to human antibodies.

Briefly, chimeric antibodies may be produced by isolating the MAb-encoding DNA sequences from a desired hybridoma, excising the portion of the murine DNA which is not required to encode the antigen-binding domains, and replacing such DNA sequences with corresponding human DNA sequences. This has been done in two alternative ways. Firstly, the complete murine variable or V region DNA of each chain can be appropriately joined to human constant or C region DNA sequences. The resultant DNAs encode polypeptides with a murine V and human C domains. Examples are provided by Morrison et al, 1984, Proc. Natl. Acad, Sci. USA 81:6851 and Liu et al, 1987, J. Immunol. 139:3521. The antibody V regions are known to encode the antigen-binding portions of the antibody, and the C regions encode the biological effector functions, such as complement fixation. In the second approach, the portions of the murine V regions thought to encode the 'antigen-binding' specificity, or complementarily-determining regions (CDRs) are identified, and the same CDRs are used to replace the human CDRs of human V regions linked to human C regions. These are 'CDR-swap' antibodies, and examples are provided by Jones et al, 1986, Nature 321:522; Verhoeyen et al, 1988, Nature 332:323; and Reichmann et al, 1988, Nature 332:323. The resultant DNAs obtained by either approach thus encode "humanized" heavy and light chains.

While such genetically engineered antibodies may overcome limitations on the use of murine MAbs, expression of the chimeric DNAs encoding such MAbs or even of cloned murine MAb genes is still problematic. In one approach the DNAs are introduced into murine hybridoma or myeloma cells for heterologous expression. However, such methods have met with only limited success, in large part because of the disappointingly low expression levels achieved thus far. Thus, a continuing need exists for a method for heteroloqous expression of antibody-encoding DNAs. One object of this invention is to provide an improved heterologous expression system for such DNAs which affords high levels of expression of antibodies, preferably chimeric antibodies.

Heterologous gene expression is typically accomplished by introducing the desired gene (or DNA encoding the desired protein) into a host cell in association with an amplifiable marker such as a gene encoding dihydrofolate reductase (DHFR). The transfected or transformed host cells are then iteratively subjected to increasing selective pressure such that the number of copies of the marker gene and the associated desired gene are increased. Where the marker is a DHFR gene, the selective agent is methotrexate (MTX), as is well known in the art. However, where heavy and light chain antibody genes are so introduced into a host cell, no practical method exists to ensure that both genes are appropriately amplified. It should be noted that if expression of one chain predominates, then the expression level of the other chain can limit the amount of antibody actually produced. Additionally, heavy chain expression in the absence of light chain expression may be deleterious to the producing cells. Heavy chain toxicity is discussed in Kohler, G, 1980, Proc. Natl. Acad. Sci. USA 77:2197 and Haas and Wabl, 1984, ibid. 81:7185.

We have found that high expression levels for antibodies depends in part on differentially amplifying the heavy and light chain DNAs to optimize the relative gene copy numbers of the heavy and light chain DNAS. In the practice of this invention, such optimization of relative gene copy number and thus the relative expression levels may be conveniently achieved by introducing the heavy chain and light chain DNAs respectively associated with different amplifiable markers, presumably into different chromosomal locations when the introduced DNA is chromosomally integrated. The heavy chain DNA and the light chain DNA are then separately amplified by application of selective conditions for the respective markers until appropriate optimization of gene expression is achieved.

By way of example, the heavy chain-encoding DNA may be linked to an adenosine deaminase (ADA) gene and the light chain-encoding DNA linked to a DHFR gene. Each of the antibody genes with its respective marker gene is then introduced into the host cells, preferably Chinese Hamster Ovary (CHO) cells by conventional methods. For example, each set of DNA may be introduced into separate CHO cells, e.g. by electroporation, and the resultant transformants fused. The ADA$^+$, DHFR$^+$ CHO cells so obtained contain the heavy chain DNA associated with an ADA gene and the light chain DNA associated with a DHFR gene, each of which DNAs is then specifically amplified by treatment with iteratively increasing amounts of MTX (amplifies light chain DNA, but not heavy chain DNA) and 2'-deoxycoformycin (dCF, amplifies heavy chain DNA but not light chain DNA). During the course of amplification the host cells are analyzed for antibody production (by ELISA). Cells so amplified for optimized antibody production were found to produce MAbs which retained the specific hapten binding characteristics of the parental MAb and which bind complement. Expression levels of about 60 µg/$10^6$ cells/48 hrs have been obtained, which may be even further improved by additional rounds of amplification. So far as we are aware, efficient production of antibodies in non-lymphoid cells has never been demonstrated heretofore.

It should be noted that the DNAs encoding the respective chains may be cDNA or genomic DNA. It should also be noted that this invention should be useful for the production not just of cloned antibodies but also of genetically engineered antibodies such as CDR-swapped antibodies as previously mentioned, and in addition, genetically engineered antibody fragments or derivatives such as $F_v$, Fab, $F(ab)'_2$ fragments using truncated DNAs and chimeric proteins such as Fab-enzyme and Fab-toxin fusion proteins. Thus, this approach will also be of general value in the production of hetero-dimeric molecules, other than complete antibodies. Examples include other forms of genetically-engineered antibodies, such as Fab and $F(ab)_2'$ forms, and antigen-binding portions, such as a Fab, linked to non-antibody peptide sequences. Examples of the genetic engineering of such molecules are found in Newberger et al, 1984, Nature 312:604; Skerra and Pluckthun, 1988, Science 240:1038; Better et al, 1988, Science 240:1041 and Reichmann et al, 1988, J. Mol. Biol. 203:825.

DETAILED DESCRIPTION OF THE INVENTION

I. Production of Hybridoma Cells

Hybridoma cell lines producing a desired antibody may be produced by conventional methods such as the well known methods of Kohler and Milstein. Briefly, an animal, preferably a rodent such as a Balb/C mouse is immunized and later re-immunized (boosted) with the desired immunogen, with an adjuvant as desired, as is well known in the art. Assaying the serum of the animal by conventional methods such as a specific ELISA reveals whether the animal is producing an antibody of the desired affinity and avidity. An immunized animal having an appropriate titer of the desired antibody is sacrificed and its spleen removed. The spleen cells are then carefully separated and fused with a suitable myeloma cell line by conventional procedures or otherwise-immortalized, as is also well known in the art. The immortalized cells producing the desired antibody are then identified by routine, conventional screening and are then subcloned as desired.

II. Cloning Heavy and Light Chain-Encoding DNAs

Methods for cloning immunoglobulin heavy and light chains is well known in the art. See e.g. Beidler et al, 1988, J. Immunol. 141:4053. (genomic) and Liu et al, 1987, Proc. Natl. Acad. Sci. USA 84:3439 (cDNA). Briefly, cDNA or genomic libraries are constructed for the RNA or genomic DNA, respectively, from hybridomas producing a specific antibody of interest, as is known in the art. The immunoglobulin clones from such libraries can be identified by hybridization to DNA or oligonucleotide probes specific for $J_H$ or $C_H$ sequences for the heavy chain clones, or $J_L$ or $C_L$ sequences for the light chain clones. The positive clones are then further characterized by conventional restriction endonuclease site mapping and nucleotide sequencing.

III. Expression Vector Construction

Any conventional eukaryotic, preferably mammalian, expression vectors designed for high expression levels, of which many are known in the art, may be used in the practice of this invention. However, in the practice of this invention the expression vector for the light chain antibody DNA contains or is cotransfected with a first selectable, amplifiable marker gene while the expression vector for the heavy chain antibody DNA contains or is cotransfected with a second selectable, amplifiable marker. The two selectable, amplifiable markers must be differentially amplifiable, i.e. must each be susceptible to amplification under conditions which do not result in amplification of the other.

The eukaryotic cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., J. Mol. Biol., 159:601-621 (1982); Kaufman, Proc Natl. Acad. Sci. 82:689-693 (1985). Eukaryotic expression vectors useful in practicing this invention may also contain inducible promoters or comprise inducible expression systems as are known in the art.

pMT2 and pMT3SVA are exemplary expression vectors which are described below. Both vectors contain an SV40 origin of replication and enhancer, adenovirus major late promoter and tripartite leader sequence, a cloning site followed by an SV40 polyadenylation site, the adenovirus VA I gene, E. coli origin of replication and an ampicillin resistance gene for bacterial selection. PMT2 further contains a DHFR gene between the cloning site and the polyadenylation signal, while pMT3SVA contains an adenosine deaminase (ADA) gene under the expression control of the SV40 early promoter. While both of these vectors contain appropriate selectable, amplifiable markers, it should be understood that separate vectors containing the markers may be cotransfected or cotransformed by conventional means with the respective heavy and light chain DNAs.

IV. Production of Transformed Cell Lines

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, both by conventional methods, CHO (Chinese Hamster Ovary) cells are currently preferred. Other usable mammalian cell lines include HeLa, human 293 cells, COS-1 monkey cells, melanoma cell lines such as Bowes cells, mouse L-929 cells, 3T3 lines derived from Swiss, Balb/c or NIH mice, BHK or HaK hamster cell lines and the like, as well as lymphocyte derived cell lines such as the murine hybridoma SP2/0-Ag14 or murine myeloma cells such as P3.653 and J558L or Abelson murine leukemia virus transformed pre-B lymphocytes.

The expression vectors may be introduced into the host cells by purely conventional methods, of which several are known in the art. Electroporation has been found to be particularly useful.

Stable transformants may then be screened for the presence and relative amount of incorporated antibody DNA and corresponding mRNA and polypeptide synthesis by standard methods. For example, the presence of the DNA encoding the desired antibody chain may be detected by standard procedures such as Southern blotting, the corresponding mRNA by Northern blotting and the protein thereby encoded by Western blotting.

It should be appreciated that the two antibody genes may be introduced serially into the same host cells, or may be introduced in parallel into separate host cells. In the former case, the antibody genes would be transfected separately, and the transfectants after the first of the two transfections, may or may not be selected in iteratively increasing amounts of the appropriate selective agent, prior to the second transfection. In the latter case, the two transfectants may be fused by conventional means to produce a cell containing and capable of expressing both antibody chains, as well as both selectable markers to facilitate isolation of hybrid cells, as ex exemplified in the Examples which follow. One of the parental cells of a fusion may be exposed to ionizing radiation before the fusion event. In addition, both heavy and light chain DNAs may be co-transfected with a single selectable, amplifiable marker, and the transfectants then passaged in iteratively increasing amounts of the selective agent. Once the relative levels of the heavy and light chains expressed in such a transfectant has been determined, a DNA encoding the chain found in limiting amounts can then be transfected into the cell, linked to a different selectable, amplifiable marker. The expression level for that chain can then be increased by iterative amplification as previously described.

V. Specific Amplification

Specific and independent amplification of the two DNAs may be readily accomplished using conventional amplification procedures appropriate for each of the respective markers. See e.g. published International Application WO 88/08035 for an exemplary description of independently amplifying a first gene linked to a DHFR gene and a second gene linked to an ADA gene. Other selectable, amplifiable markers can also be used, and examples are reviewed in Kaufman, R. J., *Genetic Engineering,* 9:155, J. K. Setlow, ed. (Plenum Publishing Corp.) 1987.

VI. Characterization of MAbs

The MAbs so produced by the amplified cell lines can be characterized by standard immunochemical techniques, including SDS-PAGE, Western blotting and immunoprecipitation of intrinsically $^{35}$S-methionine-labeled proteins. The levels of heavy and light chains produced can be quantitated by ELISAs, and binding to solid-phase antigens can be demonstrated by ELISA. The binding characteristics of the antibodies can also be studied in similar antigen-binding ELISAs in the presence of varying concentrations of free antigen. The effector functions of the antibodies can be characterized by standard techniques, e.g. for complement fixation and antibody-dependent cellular cytotoxicity.

EXAMPLES

Example 1

B1-8 hybridoma, its αNP MAb and DNAs encoding the heavy (μ) and light (λ) chains of the αNP MAb The B1-8 hybridoma cell line is a fusion of a mouse splenocyte and a murine myeloma cell line which produces an IgM antibody directed to the hapten, 4-hydroxy-3-nitro-phenyl acetate, (NP). Those MAbs have been found to bind to 4-hydroxy-5-iodo-3-nitro-phenyl acetate (NIP) with greater affinity than to the immunogen, NP, a characteristic generally termed "heterocliticity".

The heavy and light chain cDNAs have been cloned from the B1-8 hybridoma cell line and are publicly available from Dr. A. Bothwell of Yale University. The μ chain DNA and the λ chain DNA can each be conveniently isolated as restriction fragments, as described below.

Example 2

Expression Vector Construction

A. The μ chain cDNA can be cloned into plasmid pMT3SVA as follows to produce pMT3Aμ, in which expression of the μ gene is controlled by the adenovirus major late promoter and in which the μ gene is linked to an ADA transcription unit wherein ADA expression is controlled by the SV40 early promoter and enhancer.

The heavy chain expression plasmid can be constructed with the μ heavy chain cDNA of pABμ-11 (Bothwell et al, 1981, Cell 24:625). The μ cDNA may be isolated and prepared for cloning into the Eco RI site of the expression vector pMT3SVA as follows. pABμ-11 is digested to completion with Bgl_II, and then a partial Pst I digestion is performed. One resulting BgI II-Pst I fragment of approximately 1 kb should contain the complete 3' end of the cDNA and can be purified from a low-melt agarose gel. This fragment can then be ligated into Bam HI and Pst I digested Bluescript plasmid (Stratagene, La Jolla, Calif.), and transformed into *E. coil* DH5. The resultant transformants can be screened by restriction enzyme digestion of individual DNA preparations. The desired clone, with the 3' end of the μ cDNA cloned into Bluescript is called pBμ3'. A complete Pst I and Bam HI digestion of pABμ-11 will generate a Pst I-Bam HI fragment of approximately 870 bp, that can be purified by elution from a low-melt agarose gel. This fragment, called μ5', contains the 5' end of the μ cDNA, with the exception of the leader sequence. Another fragment, called μ3', can be prepared from pBμ3', by digestion with Bam HI and Eco RI, and elution from a low-melt agarose gel. This fragment of approximately 1 kb contains the 3'μ sequence derived from pABμ-11, with an Eco RI site at the 3' end of the Bluescript polylinker sequence. Fragments μ5' and μ3' can be ligated with Eco RI-digested pMT3SVA, and two synthetic oligodeoxyribo-nucleotides, to reconstruct the leader sequence. The sequences of exemplary synthetic oligodeoxyribonucleotides are as follows:

```
                                          (SEQ ID NO. 1)
5'- AATTCGTAATGGGATGGAGCTGTATCATGCTCTTCTTGGC-
AGCAACAGCTACAGGTGTCCACTCCCAGGTCCAACTGCA -3'
and
                                          (SEQ ID NO. 2)
5'- GTTGACCTGGGAGTGGACACCTGTAGCTGTTGCTGCCAAGAAGA-
GCATGATACAGCTCCATCCCATTAG -3'
```

The ligation products can be transformed into *E. coli* DH5, and transformants screened by colony hybridization to one of these two oligodeoxyribonucleotides labeled with $^{32}$P, using standard procedures. Positive colonies can be characterized further with restriction enzyme digestion analysis of DNA preparations. Digestions with Sal I and enzymes that cut in the cDNA, such as Bgl II and Bam HI can be used to orientate the insert cloned into the vector, for a unique Sal I site is positioned 3' to the Eco RI site in pMT3SVA.

The μcDNA insert used in these studies is also derived from pABμ-11, and closely resembles the example above. It was called pMT3Aμf.

B. The λ chain is introduced into an expression vector to produce pAdλ, in which expression of the λ gene is present in a bicistronic transcription unit followed by a DHFR gene, both under the expression control of the adenovirus major late promoter and SV40 enhancer.

The mouse immunoglobin λ, light chain cDNA used was derived from pABλ₁-15 (Bothwell et al., 1982, Nature 298:380). Initially the Pst I fragment from this plasmid bearing the λ₁ cDNA was cloned into the Pst I site of pSP65N, to give pλ₁-3. This vector, pSP65N, is derived from the pSP65 by digestion with Hind III, enzymatic 'filling-in' of the Hind III cohesive ends, and ligation with Not I linkers. The ligation products were digested with Not I, and religated to generate pSP65N. pSP65 can be purchased from Promega Biotec. The orientation of the λ₁ cDNA insert in pλ₁-3 was found to be such that the vector polylinker Sal I site is at the 3' end of the insert.

pλ₁-3 was digested with Fok I and Sal I, and the two novel bands of approximately 307 bp. (I) and 550 bp (II) were excised from a low-melt agarose gel, and purified. (I) represents the 5' Fok I—Fok I fragment consisting of codon −15 to codon 87 (numbering as in Bothwell et al., 1982, Nature 298:380). (II) represents codon 87 to the 3' end of the coding region, the remainder of the 3' end of the insert, and extending to the vector Sal I site.

The expression vector used was derived from pMT2DGR. This plasmid was digested with Sal I and Xho I, and the desired vector fragment was distinguished from the other fragment bearing factor VIII-related sequences on a low-melt agarose gel, and the vector fragment was excised and purified. To create pADλ₁, the pMT2DGR-derived vector fragment was ligated with fragments (I) and (II), and two synthetic oligodeoxyribonucleotides of the following sequence:

5'-TCGACGCCATGGCCTGGATT-3' (SEQ ID NO. 3), and

5'-GTGAAATCCAGGCCATGGCCG-3' (SEQ ID NO. 4).

These synthetic sequences annealed to each other, and to the Fok I cohesive end at the 5' end of (I). Their nucleotide sequence reconstructs the 5' end of the coding region and creates a small, 5' untranslated region. The ligation products were transformed into *E. coli* DH5, and the desired recombinants identified by restriction enzyme digestion of small-scale DNA preparations from individual transformants. In addition, pAdλ₁ was later transfected by the DEAE-dextran procedure, into COS-1 cells, and shown to produce a polypeptide of the correct molecular weight and immunoreactive with goat anti-mouse λ antisera (from Southern Biotechnology Associates) on western blot analysis of transfected cell extracts.

Example 3

Transformation and amplification of CHO host cells pMT3Aμf and pAdλ₁ were separately electroporated into separate pools of CHO DUKX cells (which are dhfr⁻). Pools of transfected clones were made and selected in increasing concentrations of dCF or MTX, respectively. Two pools selected at 3 μM dCF (μ) or 50 nM MTX (λ) were fused by conventional means in polyethylene glycol, and ADA⁺ DHFR⁺ cells were selected up to 3 μM dCF and 50 nM MTX. The cells were then further selected up to 3 μM dCF and 200 nM MTX and 10 μM dCF and 50 nM MTX. It was found that only the increased concentration of dCF led to an increase in the amount of functional Ab as determined by a hapten-binding ELISA. This correlated with an increase in the amount of heavy chain produced, and therefore it is concluded that the amount of heavy chain was limiting the amount of functional antibody produced. The 10 μM dCF and 50 nM MTX pool was then further selected at up to 40 μM dCF and 50 nM MTX. At this stage, clones were obtained by plating the cells at low density, and after an appropriate period of growth, macroscopic colonies were cloned out using cloning cylinders as is well known in the art.

The levels of μ, λ and NP-binding MAb produced at different levels of selection were measured by ELISAs based upon standard procedures, as described in Voller, A. et al. (1979), the Enzyme Linked Immunosorbent Assay (ELISA), Dynatech Europe, Borough House, Rue de Pre, Guernsey, UK; Bos, et al., 1981, *J. Immunoassay* 2:187; Wood et al., 1984, *Nucleic Acids Research* 12:3937; and Boss et al., 1984, *Nucleic Acids Research* 12:3791.

Example 4

Characterization of the CHO MAb so Produced

The CHO cells were cultured in alpha medium containing 10% (by volume) heat-inactivated, dialyzed fetal calf serum and 10 μg/ml penicillin, 10 μg/ml streptomycin and 1 mM L-glutamine with the selective agents. Selection for DHFR⁺ cells was initially carried out in this medium, and then selection was increased with iteratively increasing concentrations of methotrexate.

When using ADA section, the cells were cultured in media supplemented with 0.05 mM L-alanosine, 1 mM uridine and 1.1 mM adenosine, in addition to dCF. Descriptions of the types of culture and selection procedures employed are given in Kaufman et al., 1987, *Proc. Natl. Acad. Sci. USA* 83:3136; Kaufman et al., 1987, *EMBO J.* 6:187; and Kaufman et al., 1985, *Mol. Cell Biol.* 5:1750. The medium for selection of ADA⁺ DHFR⁺ cells contained 10% (v/v) dialyzed fetal calf serum (heat inactivated), 10 μg/ml each of penicillin and streptomycin, 1 mM L-glutamine, 0.05 mM L-alanosine, 1 mM uridine, 1.1 mM adenosine, dCF and methotrexate.

The CHO MAbs were found to bind immobilized NP, and this binding could be competed out with 30 μM free NP. The CHO MAb was found to have a greater affinity for NIP than for NP, demonstrating the retention of the parental MAb's heterocliticity. Furthermore, the CHO MAbs were found to be polymeric IgMs and to produce plaques in an NP-plaque assay—a qualitative measure of complement fixation. Dresser, D. W., and Greaves, M. F., (1983) in *Handbook of Experimental Immunology*, D. M. Weir, ed. (Blackwell Scientific Publications, Oxford), p271; O'Hara, R. M., Jr., et al., (1988) *Cell. Immunol.* 116:423. Thus, in each of the parameters measured (hapten binding, complement fixation, and heterocliticity), the CHO MAbs were found to be strikingly similar to the parental B1-8 MAbs. The synthesis of these immunoglobin light and heavy chains were also studied by western blotting, and pulse-chase labelling with L-³⁵S-methionine and immunoprecipitation. The heterologously expressed polypeptides were found to resemble closely the hybridoma-produced antibody polypeptides.

What is claimed is:

1. A method of optimizing the expression level of an antibody or a fragment thereof which comprises:
    (a) producing eukaryotic host cells containing and capable of expressing a first DNA sequence encoding at least an antibody heavy chain or an antigen binding portion thereof, said first DNA sequence being associated with a first heterologous selectable amplifiable marker gene, and a second DNA sequence encoding at least an antibody light chain or an antigen binding portion thereof, said second DNA sequence being associated with a second heterologous selectable amplifiable marker gene;
    (b) culturing said host cells in a suitable culture medium;
    (c) differentially amplifying said first and second DNA sequences with appropriate selective agents to allow maximized production of said antibody or fragment thereof
    (d) choosing a host cell that produces a desired amount of antibody.

2. The method of claim 1, wherein the antibody expression level is at least about 60 µg/10⁶ cells/48 hrs.

3. The method of claim 1, wherein the first heterologous selectable amplifiable marker gene is an ADA gene or a DHFR gene.

4. The method of claim 1, wherein the second heterologous selectable amplifiable marker gene is an ADA gene or a DHFR gene.

5. The method of claim 1, wherein the first heterologous selectable amplifiable marker gene is a DHFR gene and the second heterologous selectable amplifiable marker gene is an ADA gene.

6. The method of claim 1, wherein the first heterologous selectable amplifiable marker gene is an ADA gene and the second heterologous selectable amplifiable marker gene is a DHFR gene.

7. The method of claim 1, wherein the antibody or fragment thereof is a monoclonal antibody.

8. The method of claim 1, wherein the antibody or fragment thereof is a genetically engineered antibody.

9. The method of claim 8, wherein the genetically engineered antibody or fragment thereof is a chimeric, humanized or a CDR-swapped antibody.

10. The method of claim 1, wherein the antibody fragment is selected from the group consisting of Fv, Fab, and F(ab)'2.

11. The method of claim 1, wherein the antibody or fragment thereof is a chimeric protein.

12. The method of claim 11, wherein the chimeric protein comprises an Fab linked to a non-antibody sequence.

13. The method of claim 11, wherein the chimeric protein is an Fab-enzyme or an Fab-toxin.

14. The method of claim 1, wherein the host cells are produced by fusing at least two cells.

15. The method of claim 1, wherein the host cells are mammalian cells.

16. The method of claim 1, wherein the host cells are non-lymphoid cells.

17. The method of claim 16, wherein the non-lymphoid cells are selected from the group consisting of Chinese Hamster Ovary (CHO) cells, HeLa cells, human 293 cells, COS monkey cells, Bowes cells, mouse L-929 cells, 3T3 cell line, BHK hamster cells, and HaK hamster cells.

18. The method of claim 16, wherein the non-lymphoid cells are CHO cells.

19. A method of optimizing expression of an antibody or fragment thereof comprising:
 (a) producing a first eukaryotic host cell containing and capable of expressing a first DNA sequence encoding at least an antibody heavy chain variable region or an antigen binding portion thereof, said first DNA sequence being associated with a heterologous selectable amplifiable marker gene;
 (b) producing a second eukaryotic host cell containing and capable of expressing a second DNA sequence encoding at least an antibody light chain variable region or an antigen binding portion thereof, said second DNA sequence being associated with a heterologous selectable amplifiable marker gene,
 (c) culturing said host cells in suitable selective culture media;
 (d) measuring the relative amounts of said first and second DNA sequences expressed;
 (e) differentially amplifying said first and said second DNA sequences with appropriate selective agent to optimize the relative gene copy number of said first and second DNA sequences;
 (f) fusing said first and second host cells; and
 (g) expressing said antibody or fragment thereof.

20. A method of optimizing expression of an antibody or fragment thereof comprising:
 (a) producing a first eukaryotic host cell containing and capable of expressing a first DNA sequence encoding at least an antibody heavy chain variable region or an antigen binding portion thereof, said first DNA sequence being associated with a heterologous selectable amplifiable marker gene;
 (b) producing a second eukaryotic host cell containing and capable of expressing a second DNA sequence encoding at least an antibody light chain variable region or an antigen binding portion thereof, said second DNA sequence being associated with a heterologous selectable amplifiable marker gene,
 (c) culturing said host cells in suitable selective culture media;
 (d) differentially amplifying said first and second DNA sequences with appropriate selective agent;
 (e) fusing said first and second host cells;
 (f) choosing a host cell that produces a desired amount of antibody; and
 (g) expressing said antibody or fragment thereof.

* * * * *

UNITED STATES PATENT AND TRADEMARK OFFICE
CERTIFICATE OF CORRECTION

PATENT NO. : 7,247,475 B2
APPLICATION NO. : 11/324255
DATED : July 24, 2007
INVENTOR(S) : Clive R. Wood and Randal J. Kaufman It is certified that error appears in the above-identified patent and that said Letters Patent is hereby corrected as shown below:

In claim 1, column 9, line 51, "thereof which" should read --thereof, which--

In claim 1, column 9, line 67, "thereof" should read --thereof; and--

Signed and Sealed this

Twentieth Day of November, 2007

JON W. DUDAS
*Director of the United States Patent and Trademark Office*